(12) United States Patent
Lim et al.

(10) Patent No.: US 10,596,302 B2
(45) Date of Patent: Mar. 24, 2020

(54) CATHETER TUBING WITH TAILORED MODULUS RESPONSE

(71) Applicant: Becton, Dickinson and Company, Franklin Lakes, NJ (US)

(72) Inventors: Lisa Lim, Sandy, UT (US); Theresa Hermel-Davidock, Newton, NJ (US); Marc W. Weimer, South Jordan, UT (US); Jonathan Karl Burkholz, Salt Lake City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 117 days.

(21) Appl. No.: 15/489,109

(22) Filed: Apr. 17, 2017

(65) Prior Publication Data

US 2018/0296731 A1 Oct. 18, 2018

(51) Int. Cl.
*A61L 29/04* (2006.01)
*A61L 29/18* (2006.01)
(Continued)

(52) U.S. Cl.
CPC ............. *A61L 29/049* (2013.01); *A61L 29/02* (2013.01); *A61L 29/18* (2013.01);
(Continued)

(58) Field of Classification Search
CPC .... A61M 2025/0059; A61M 2025/006; A61M 2025/0064; A61M 2025/0065; A61M 25/0012; A61M 25/0017; A61M 25/0021; A61M 25/0054; A61L 29/06; A61L 2300/404; A61L 2300/42; A61L 29/02; A61L 29/049; A61L 29/14; A61L 29/16; A61L 29/18; C08L 75/04; C08G 18/3206;
(Continued)

(56) References Cited

U.S. PATENT DOCUMENTS

| 4,647,643 A | 3/1987 | Zdrahala |
| 4,935,480 A | 6/1990 | Zdrahala |

(Continued)

FOREIGN PATENT DOCUMENTS

| DE | 19619327 A1 | 11/1997 |
| EP | 0448886 A1 | 10/1991 |

(Continued)

OTHER PUBLICATIONS

PCT International Search Report and Written Opinion in PCT/US2018/026250 dated Jul. 6, 2018, 16 pages.

*Primary Examiner* — Quynh-Nhu H. Vu
(74) *Attorney, Agent, or Firm* — Servilla Whitney LLC (57) ABSTRACT

Catheter tubing comprises: an elongate body comprising a base thermoplastic polyurethane; and a compounded thermoplastic polyurethane co-extruded with the base thermoplastic polyurethane to provide a section of catheter tubing discrete from the elongate body, the compounded thermoplastic polyurethane comprising a thermoplastic polyurethane and a radiopaque material, wherein the catheter tubing comprises a first elastic modulus under first conditions prior to entry into a patient; and wherein when exposed to second conditions comprising two or more in vivo stimuli for a duration of time the catheter tubing comprises a second elastic modulus that is not more than fifty percent of the first modulus.

21 Claims, 1 Drawing Sheet

(51) Int. Cl.
*A61L 29/02* (2006.01)
*A61M 25/00* (2006.01)

(52) U.S. Cl.
CPC .... *A61M 25/0017* (2013.01); *A61M 25/0021* (2013.01); *A61M 2025/006* (2013.01)

(58) Field of Classification Search
CPC ............ C08G 18/4854; C08G 18/6674; C08G 18/7671
See application file for complete search history.

(56) References Cited

U.S. PATENT DOCUMENTS

| | | |
|---|---|---|
| 4,939,007 A | 7/1990 | Hu |
| 5,059,269 A | 10/1991 | Hu |
| 5,061,254 A * | 10/1991 | Karakelle ............... A61L 29/06 604/265 |
| 5,159,050 A | 10/1992 | Onwumere |
| 5,159,051 A | 10/1992 | Onwumere |
| 5,226,899 A | 7/1993 | Lee |
| 5,250,649 A | 10/1993 | Onwumere |
| 5,266,669 A | 11/1993 | Onwunaka |
| 5,281,677 A | 1/1994 | Onwunaka |
| 5,453,099 A * | 9/1995 | Lee ........................ A61L 29/085 604/264 |
| 5,545,708 A * | 8/1996 | Onwunaka ............... A61L 29/06 264/165 |
| 6,342,047 B1 * | 1/2002 | Urakawa ............... A61L 29/049 525/458 |

FOREIGN PATENT DOCUMENTS

| | | |
|---|---|---|
| EP | 0472413 A2 | 2/1992 |
| EP | 0824932 A2 | 2/1998 |
| EP | 0914836 A2 | 5/1999 |
| EP | 0962227 A1 | 12/1999 |
| WO | 20061042739 A1 | 4/2006 |

* cited by examiner

CATHETER TUBING WITH TAILORED MODULUS RESPONSE

TECHNICAL FIELD

The present disclosure relates generally to devices, systems, and methods in the medical field including catheter tubing comprising a thermoplastic polyurethane having a softening profile where the tubing softens only upon exposure to in vivo stimuli.

BACKGROUND

Thermoplastic polyurethane materials are some of the most commonly used biomaterial polymer for various medical applications. Some thermoplastic polyurethane materials are stiff and their flexibility may not be controllable. This limits their use in many types of polyurethane medical applications, especially for long-term medical uses. In some cases, these materials are not able to maintain their original stiffness or other physical property and their physical properties change too quickly.

For medication infusion or injection, an invasive medical device is typically used to create a fluid channel from a medication reservoir to the patient, usually to vascular vessels or subcutaneous tissue. To ensure success of insertion to the body tissue of a target area, the entry portion of the device needs to be stiff enough for minimum pain. Intravascular catheters, for example, are currently utilized in a wide variety of minimally invasive medical procedures. Generally, an intravascular catheter allows a clinician to remotely perform a medical procedure by inserting the catheter into the patient's vascular system. Typically, the practice is to insert a flexible catheter tube into a vein and leave the catheter tube in such a position for purposes such as periodically administering fluids, transfusions and medication, collecting of blood samples, and the like. The catheter tube may remain in place for days or weeks at a time. After the distal portion of the catheter tube has entered the patient's vascular system, the clinician may advance the distal tip forward by applying longitudinal forces to the proximal portion of the catheter and bend force to the catheter tube body. For the catheter tubing to effectively communicate these longitudinal forces, it is desirable that the catheter tube has a high level of pushability, which can be translated to a material property of high stiffness of catheter tube. In some countries, nursing practices prior to insertion of IV catheter include pre-priming the IV catheters in 25° C. (or ambient) saline, which can cause the tubing to soften such that insertion becomes difficult. Once reaching the tissue, such as a blood vessel, the part of the device that remains in the tissue needs to be soft enough to minimize potential complications, such as mechanical phlebitis, and improve patient comfort. In some instances, a catheter may cause phlebitis, which is an inflammation of a vein, due to local trauma to the vein in which the catheter is inserted. Harder catheters in the vein can be more likely to cause such trauma.

There remains a need for polyurethanes for catheter manufacture that are stiff under ambient conditions for catheter insertion but which becomes soft and pliable for positioning and indwelling only upon exposure to more than one in vivo stimuli.

SUMMARY

Provided are medical devices, for example, catheter tubing. Non-limiting examples of catheter tubing include: peripheral intravenous (IV) catheters; intravascular catheters; central venous catheters including tri-lumen, bi-lumen, and single lumen; midline catheters; and urinary catheters. Vascular access devices may use catheter tubing as disclosed herein in conjunction with one or more components such as needles and/or guidewires.

In an embodiment, a catheter tubing comprises: an elongate body comprising a base thermoplastic polyurethane; and a compounded thermoplastic polyurethane co-extruded with the base thermoplastic polyurethane to provide a section of catheter tubing discrete from the elongate body, the compounded thermoplastic polyurethane comprising a thermoplastic polyurethane and a radiopaque material; wherein the catheter tubing comprises a first elastic modulus under first conditions prior to entry into a patient; and wherein when exposed to second conditions comprising two or more in vivo stimuli for a time, the catheter tubing comprises a second elastic modulus that is not more than fifty percent of the first modulus.

The thermoplastic polyurethane of the compounded thermoplastic polyurethane may be a different formulation from the base thermoplastic polyurethane. The section discrete from the elongate body may comprise one or more elongate stripes comprising the compounded thermoplastic polyurethane, integrally formed with the elongate body. The catheter tubing of may have a cross-sectional area that comprises the base thermoplastic polyurethane in an amount in the range of 60% to 80% and the compounded thermoplastic polyurethane in an amount in the range of 20% to 40%.

The first conditions may comprise: a temperature in the range of 20 to 30° C. and a relative humidity in the range of 0 to 90%. The first elastic modulus may be at least 1300 MPa. The first elastic modulus may be the range of 1300 to 2200 MPa.

The two or more in vivo stimuli of the second conditions may comprise a temperature in the range of about 36 to about 40° C., and one or more of: saline, plasma, white blood cells, platelets, red blood cells, water, absence of light, antibodies, and enzymes. The second elastic modulus may be at most 650 MPa, 400 MPa, 200 MPa, or 100 MPa. The second elastic modulus may be in the range of 10 to 650 MPa, 10 to 400 MPa, 10 to 200 MPa, or 10 to 100 MPa. The second elastic modulus may be reached after exposure to the second conditions for about 30 minutes or less. The second elastic modulus may be reached after exposure to the second conditions for about 5 to about 10 minutes.

The radiopaque material of the compounded thermoplastic polyurethane may comprise bismuth oxychloride (BiOCl), bismuth trioxide ($Bi_2O_3$), bismuth subcarbonate ($Bi_2O_2CO_3$), barium sulfate ($BaSO_4$), tungsten (W), or combinations thereof.

The base thermoplastic polyurethane, the compounded thermoplastic polyurethane, or both may further comprise an antithrombogenic agent, an antimicrobial agent, a lubricant, a colorant, an active pharmaceutical, or combinations thereof.

In a detailed aspect, a catheter tubing comprises: an elongate body comprising a base thermoplastic polyurethane that is a product from a reaction of: a diisocyanate, a diol chain extender, at least one polyglycol, and optionally, an amine-terminated polyether, the base thermoplastic polyurethane optionally further comprising an antithrombogenic agent, an antimicrobial agent, a lubricant, a colorant, an active pharmaceutical, or combinations thereof; and one or more elongate stripes co-extruded with the base thermoplastic polyurethane, the elongate stripes comprising a compounded thermoplastic polyurethane comprising a thermoplastic polyurethane and a radiopaque material; wherein the catheter tubing comprises a first elastic modulus under first conditions prior to entry into a patient; and wherein when exposed to second conditions comprising two or more in vivo stimuli for a time, the catheter tubing comprises a second elastic modulus that is not more than fifty percent of the first modulus.

The first conditions may comprise: a temperature in the range of 20 to 30° C. and a relative humidity in the range of 0 to 90% and the two or more in vivo stimuli of the second conditions comprise a temperature in the range of about 36 to about 40° C., and one or more of: saline, plasma, white blood cells, platelets, red blood cells, water, absence of light, antibodies, and enzymes.

The first elastic modulus may be in the range of 1300 to 2200 MPa and the second elastic modulus is the range of 10 to 650 MPa, 10 to 400 MPa, 10 to 200 MPa, or 10 to 100 MPa.

The second elastic modulus may be reached after exposure to the second conditions for about 30 minutes or less. The second elastic modulus may be reached after exposure to the second conditions for about 5 to about 10 minutes.

An aspect is a vascular access device comprising any catheter tubing disclosed herein in combination with one or more components, wherein the vascular access device is selected from the group consisting of: a central venous catheter, a peripherally-inserted central catheter, a midline catheter, and a peripheral intravenous catheter.

An aspect is a method of making a medical device including a catheter tubing comprising: designing an elongate body having a section of catheter tubing discrete from the elongate body to form the catheter tubing such that the catheter tubing comprises a first elastic modulus under first conditions prior to entry into a patient; and wherein when exposed to second conditions comprising two or more in vivo stimuli for a time, the catheter tubing comprises a second elastic modulus that is not more than fifty percent of the first modulus.

The designing of the elongate body having the section of catheter tubing discrete from the elongate body may comprise: providing a base polyurethane; providing a compounded polyurethane comprising a thermoplastic polyurethane and a radiopaque material; and co-extruding the base polyurethane and the compounded polyurethane to form the elongate body of the base polyurethane and the section discrete from the elongate body of the compounded thermoplastic polyurethane. The method may further comprise combining the catheter tubing with one or more components to form the medical device. The one or more components may include a needle and the medical device may be a vascular access device. The vascular access device may be selected from the group consisting of: a central venous catheter, a peripherally-inserted central catheter, a midline catheter, and a peripheral intravenous catheter.

A further aspect is a method of delivering a medical fluid to a patient comprising: obtaining a catheter tubing; inserting the catheter tubing into a patient under first conditions when the catheter tubing comprises a first elastic modulus; and indwelling the catheter tubing for a duration under second conditions when the catheter tubing is exposed to two or more in vivo stimuli and the catheter tubing comprises a second elastic modulus that is not more than fifty percent of the first modulus. The catheter tubing may comprise: an elongate body comprising a base thermoplastic polyurethane; and one or more sections discrete from the elongate body comprising a compounded polyurethane comprising a thermoplastic polyurethane and a radiopaque material.

The first conditions may comprise: a temperature in the range of 20 to 30° C. and a relative humidity in the range of 0 to 90% and the two or more in vivo stimuli of the second conditions may comprise a temperature in the range of about 36 to about 40° C., and one or more of: saline, plasma, white blood cells, platelets, red blood cells, water, absence of light, antibodies, and enzymes.

The first elastic modulus may be in the range of 1300 to 2200 MPa and the second elastic modulus may be in the range of 10 to 650 MPa, 10 to 400 MPa, 10 to 200 MPa, or 10 to 100 MPa. The second elastic modulus may be reached after exposure to the second condition for about 5 to about 10 minutes.

DETAILED DESCRIPTION

Before describing several exemplary embodiments of the invention, it is to be understood that the invention is not limited to the details of construction or process steps set forth in the following description. The invention is capable of other embodiments and of being practiced or being carried out in various ways.

Provided are medical devices, for example, catheter tubing, that provide both high inherent stiffness of polyurethane under environmental conditions and flexibility after being exposed to two or more in vivo stimuli. The devices are a composite assembly, comprising a base thermoplastic polyurethane and a compounded thermoplastic polyurethane co-extruded with the base thermoplastic polyurethane. The base thermoplastic polyurethane and the compounded thermoplastic polyurethane form discrete sections of the tubing. The compounded thermoplastic polyurethane may form one or more elongate stripes on or within a body composed of the base polyurethane. The thermoplastic polyurethane of the compounded thermoplastic polyurethane may be the same formulation as the base thermoplastic polyurethane, or it may be different depending on the application. By using a composite system, the tubing herein provides a nuanced softening profile in a way that unitary systems cannot.

Elastic modulus is a property of a thermoplastic material that indicates a degree of stiffness or softness of the material. A catheter of stiffer materials at insertion decreases the likelihood of a failure IV catheter insertion due to catheter failures such as catheter tip peel back and catheter tubing accordion. An elastic modulus of at least about 400 MPa is a non-limiting target for effective insertion. Upon insertion, softening of the materials is desirable for comfort and minimizing potential complications. An elastic modulus that is about 400 MPa may be tolerable for indwelling, but an elastic modulus that is lower than 400 MPa is desirable for indwelling. For example, relatively low elastic modulus values in the non-limiting range of less than about 100 MPa may be desired. As discussed, higher modulus for insertion is desired in combination with lower modulus for indwelling.

Advantageously, the polyurethane-based catheter tubing of the present disclosure, which has discrete sections, e.g., stripes, in combination with a body, softens to an elastic modulus after insertion and exposure to two or more in vivo stimuli that is reduced by fifty percent or more compared to the elastic modulus prior to insertion. In one or more embodiments, the tubing has modulus of 500 MPa or greater, or 1300 MPa or greater, at all environmental conditions encountered during insertions of IV catheters; however, it will decrease its modulus (for example to 650 MPa or less, or 400 MPa or less, or 200 MPa or less, or 100 MPa or less) during a relatively short duration (e.g., 30 minutes or less, 10 minutes or less, or about 5 minutes) upon exposure to multiple stimuli (such as body temperature, saline, plasma, white blood cells and platelets, red blood cells, water, absence of light, antibodies, certain enzymes, etc.) when in the vein to reduce catheter related complications like phlebitis, infiltration, and extravasation. In some countries, nursing practices prior to insertion of IV catheter include pre-priming the IV catheters in 25° C. (or ambient) saline. The catheter tubing of the present disclosure maintains a high elastic modulus (e.g., 500 MPa or greater, or 1300 MPa or greater), which is a higher modulus than current commercially available materials within expected pre-priming to insertion time range (0-10 minutes) to ensure successful insertion of the IV catheters. That is, upon exposure to only a single in vivo condition, as simulated, for example, by saline, the tubing of the present disclosure remains stiff enough for insertion. Upon entry into the body environment and exposure to a second in vivo condition, the tubing becomes softer.

Prior art in catheter tubing materials have historically focused on the compositions of polyurethane materials without recognizing particular properties of the materials properties that facilitate successful with IV catheter placement and monitoring by a clinician. Until the present disclosure, there was not consideration of properties of the materials at different environment temperature and humidity or pre-priming scenarios. The present disclosure has identified that reduction of polyurethane material modulus only when a combination of multiple stimuli that are unique in the body environment (e.g., the veins) facilitates successful with IV catheter placement and monitoring by a clinician.

Elastic modulus as used herein is the pressure at which the catheter tubing bends, measured in MPa by techniques known in the art. A Dynamic Mechanical Analyzer (DMA) from TA Instrument model Q800 may be used to measure elastic modulus.

In vivo stimulus or stimuli refer to actual or simulated condition(s) that exist in the environment of the body including but not limited to temperature in the range of about 36 to about 40° C.; exposure to: saline, plasma, white blood cells, platelets, red blood cells, water, antibodies, and enzymes; and absence of light. In vivo stimuli may be simulated by ex vivo experiments that approximate stimuli that exist in the environment of the body. This may be done, for example, by exposing tubing to a saline bath with a temperature in the range of about 36 to about 40° C. Exposure to in vivo stimulus or stimuli begins when the tubing is securely placed in vivo and achieves the temperature of the environment of the body. For simulation purposes, exposure to in vivo stimulus or stimuli begins when the tubing is under steady state in vivo conditions.

Radiopaque materials may be included in compounded polyurethanes to render them X-ray detectable. Most commonly used radiopaque fillers are one or more of: bismuth oxychloride (BiOCl), bismuth trioxide ($Bi_2O_3$), bismuth subcarbonate ($Bi_2O_2CO_3$), barium sulfate ($BaSO_4$), and tungsten (W).

Polyurethanes

Polyurethane materials disclosed herein have controlled and desirable stiffness and flexibility. The stiffness and flexibility of this polyurethane may be tailored and purposely varied to fit different practical needs. Medical devices formed of these polyurethane materials are used to create a fluid channel from a medication reservoir to a patient in need thereof, where the fluid channel may be inserted into and in fluid communication with vascular vessels, or subcutaneous tissue, where the invasive medical device comprises any of the polyurethane materials as described herein.

Thermoplastic polyurethanes (TPUs) suitable for medical devices are typically synthesized from three basic components, a diisocyanate, a polyglycol, and a chain extender, usually a low molecular weight diol, diamine, or water. If the chain extender is a diol, the polyurethane consists entirely of urethane linkages. If the extender is water or diamine, both urethane and urea linkages are present, which results in a polyurethaneurea (PUU). Inclusion of an amine-terminated polyether to the polyurethane synthesis also results in a polyurethaneurea (PUU). Device applications for thermoplastic polyurethanes include central venous catheters (CVCs), peripherally inserted central catheter (PICCs), and peripheral intravenous catheters (PIVCs). Thermoplastic polyurethanes chain extended with diols used in medical devices are disclosed in the following co-owned patents: U.S. Pat. Nos. 5,545,708; 5,226,899; 5,281,677; and 5,266,669.

Polyurethane and polyurea chemistries are based on the reactions of isocyanates with other hydrogen-containing compounds, where isocyanates are compounds having one or more isocyanate group (—N=C=O). Isocyanate compounds can be reacted with water ($H_2O$), alcohols (R—OH), carboxylic acids (R—COOH), amines ($R_x$—$NH_{(3-x)}$), ureas (R—NH—$CONH_2$), and amides (R—$CONH_2$). Certain polyurethanes may be thermoplastic elastomers (TPE), whereas other compositions may be highly cross-linked.

Thermoplastic polyurethanes comprise two-phases or microdomains conventionally termed hard segments and soft segments, and as a result are often referred to as segmented polyurethanes. The hard segments, which are generally of high crystallinity, form by localization of the portions of the polymer molecules which include the diisocyanate and chain extender(s). The soft segments, which are generally either non-crystalline or of low crystallinity, form from the polyglycol or the optional amine-terminated polyether. The hard segment content is determined by the weight percent of diisocyanate and chain extender in the polyurethane composition, and the soft segment content is the weight percent of polyglycol or polydiamine. The thermoplastic polyurethanes may be partly crystalline and/or partly elastomeric depending on the ratio of hard to soft segments. One of the factors which determine the properties of the polymer is the ratio of hard and soft segments. In general, the hard segment contributes to hardness, tensile strength, impact resistance, stiffness and modulus while the soft segment contributes to water absorption, elongation, elasticity and softness.

Polyurethane materials may be used as raw materials for catheter tubing via extrusion or molding, where the formed catheter tubing is capable of improving the success of insertion due to increased initial tubing stiffness, and/or significantly extending the catheter tubing's indwelling and reducing catheter tubing induced clinical complications because of its greater flexibility and antimicrobial activity. The medical device may have a predetermined balance of stiffness for insertion and pliability for threading through a blood vessel.

Stiffness, flexibility, and softening in response to environmental changes depend on the polyurethane's molecular structure and polymerization methods controlled by adjusting the balance of the hydrophobicity and hydrophilicity of the material. One of the solutions to control polyurethane stiffness and flexibility is to determine an appropriate balance between hydrophobicity and hydrophilicity. This may be achieved by selecting a particular type of isocyanate, polyol, chain extender, and their composition, to produce an intended combination of properties appropriate for the specific application.

A thermoplastic polyurethane may be produced by the reaction of: a diisocyanate, a diol chain extender, at least one polyglycol, and optionally, an amine-terminated polyether. The thermoplastic polyurethane may optionally further comprise an antithrombogenic agent, an antimicrobial agent, a lubricant, a colorant, an active pharmaceutical, or combinations thereof. The polyurethane may have a hard segment content between about 50% and about 70% by weight, where a hard segment is the portion(s) of the polymer molecules which include the diisocyanate and the extender components, which are generally highly crystalline due to dipole-dipole interactions and/or hydrogen bonding. In contrast, the soft segments form from the polyglycol portions between the diisocyanate of the polymer chains and generally are either amorphous or only partially crystalline due to the characteristics of the polyglycol(s).

Polymerization of the polyurethane may be a one-step bulk polymerization without requiring a catalyst or other additives.

A polyglycol is a polymer derived from an alkylene oxide containing ether-glycol linkages which contains a chain of repeating units with a distribution of a number of repeating units. Polyglycols include polyetherglycols.

A chain extender is a discrete hydroxyl- and/or amine-terminated compounds used during polymerization to impart desired properties to a polymer.

With respect to polyurethane chemistry:

$$\text{Isocyanate index} = \frac{\text{Isocyanate equivalents}}{\text{polyol equivalents}}$$

The isocyanate equivalent is defined as the weight of sample which will combine with 1 g equivalent weight of the aromatic diisocyanate. The sample is generally a polyol, amine or other compound that possesses groups capable of reacting with an isocyanate. See C. Hepburn "*Polyurethane Elastomers*" 2nd Edition, Springer, pages 42-43, (1992). In general, the polyurethane becomes harder with an increasing isocyanate index. There is, however, a point beyond which the hardness does not increase and the other physical properties begin to deteriorate. Polyurethane materials provided herein have an isocyanate index in the range of 1 to 1.4.

The diisocyanate may be an aromatic diisocyanate. In various embodiments, the aromatic isocyanate may be selected from the group consisting of 4,4'-diphenylmethane diisocyanate (MDI) (Formula I), 2,2'-dimethyl-4,4'-biphenyldiisocyanate (Formula II), 3,3'-dimethyl-4,4'-diphenyl diisocyanate (TODI) (Formula III), 2,4-toluene diisocyanate, 2,6-toluene diisocyanate (TDI), 1,5-naphthalene diisocyanate (NDI), 4,6'-xylylene diisocyanate (XDI), 3,3'-dimethyl-diphenylmethane 4,4'-diisocyanate (DMMDI), dianisidine diisocyanate (DADI), and their blends.

The at least one polyglycol may be a polytetramethylene ether glycol. The polytetramethylene ether glycol (PTMEG) may be PTMEG250, PTMEG650, PTMEG1000, PTMEG1450, PTMEG1800, PTMEG2000, and PTMEG2900. PTMEG having the formula: $HO(CH_2CH_2CH_2CH_2-O-)_nH$, which may have an average value of n in the range of 3 to 40. A blend of two or more PTMEG250, PTMEG650, PTMEG1000, PTMEG1450, PTMEG1800, PTMEG2000, and PTMEG2900 may be used such. A preferred an average molecular weight of the combination is about 1000 Da. In one or more embodiments, the polyols is a blend of two or more PTMEG having the formula: $HO(CH_2CH_2CH_2CH_2-O-)_nH$, where n has an average value in the range of 3 to 40 and an average molecular weight of the combination being 1000 Da or less.

Additional polyglycols may be present in the polyurethane material, including but not limited to: polyethylene oxide glycol (PEG), polypropylene oxide glycol (PPG), polyester glycol, silicone glycol, polycarbonate glycol, and combinations thereof. The additional polyglycols may be selected from: PEG 8000, PPG PT3000, or combinations thereof. PEG 8000 is a polyethylene glycol having a formula weight of 7,000-9,000. PPG PT3000 is a polypropylene glycol having an average molecular weight of 3,000. A polycarbonate glycol having an average molecular weight of 350 to 1000 may be used.

A diol may be linear, comprising one or more of: butane diol (BDO), ethylene glycol, diethylene glycol, triethylene glycol, 1,2-propane diol, 1,3-propane diol, 1,5-pentanediol, 1,6-hexane diol, 1,4-bis hydroxymethyl cyclohexane, hydroquinone dihydroxyethyl ether. A diol may be side-branching, comprising one or more of: 2,2-dimethyl-1,3-propanediol (NPG), 2-methyl-1,3-propanediol, 2-butyl-2-ethyl-1,3-propanediol (BEPD), 1,3-Dibromo-2,2-dimethylolpropane (BBMPD).

The polyurethane may further comprise a polyetheramine. Suitable polyetheramines include but are not limited to amine-terminated polyethers having repeating units of polyethylene oxide, polypropylene oxide or polytetramethylene oxide and having a molecular weight in the range of about 400 to 8,000. Preferred polyetheramines have polypropylene oxide repeating units. Jeffamine® D4000 is a specific polyetheramine, an amine-terminated polyoxypropylene glycol, having an average molecular weight of about 4000.

The polyurethanes described herein may be fabricated into film, tubing, and other forms by conventional thermoplastic fabricating techniques including melt casting, extrusion, molding, etc. The polyurethane described herein may be used for PICCs, PIVCs, and CVCs. The polymer may have incorporated therein, as desired, conventional stabilizers. The amounts of these materials will vary depending upon the application of the polyurethane, but they are typically present in amounts so ranging from 0.1 to 50 weight percent of the polymer.

The stiffness, flexibility and polyurethane's softening are dependent of its molecular structure and its environment. Polyurethane's flexibility can be changed by a change of its environment, and controlled by adjusting the balance of its hydrophobicity and hydrophilicity of the material. The hydrophobicity and hydrophilicity depends on its molecular structure and composition.

General Procedure for Polyurethane Synthesis

The polyurethanes discussed here were prepared by "one shot" bulk synthesis process. The polyol(s) and chain extender(s) were mixed thoroughly with vacuum stripping first and then with nitrogen gas purging for 12 to 24 hours. At ambient temperature, a calculated quantity of diisocyanate was added all at once with very vigorous stirring. Vigorous stirring was conducted, then the mixture was poured into a Teflon-lined tray and immediately placed in an oven for post curing.

TABLE 1

Exemplary Formulations of Polyurethanes with the proviso that the ingredients total 100%.

| Table 1 Reactant | 1-A by weight | 1-B by weight | 1-C by weight |
|---|---|---|---|
| Diisocyanate | 30-60% | 35-55% | 40-50% |
| Total Polyglycol | 10-44.9% | 15-39.9 | 22-34.9 |
| Polyetheramine MW230-4000 | 0-30% | 0-25% | 0-20% |
| Diol Chain Extender | 0.1-25% | 5-20% | 12-18% |
| Hard Segment % | 50-75% | 52-68% | 55-65% |

TABLE 2

Exemplary Formulations of Compounded Polyurethanes with the proviso that the ingredients total 100%.

| Table 2 Reactant | 2-A by weight | 2-B by weight | 2-C by weight |
|---|---|---|---|
| Diisocyanate | 20-45% | 25-40% | 29-39% |
| Total Polyglycol | 10-39.9% | 11-35.9 | 12-29.9 |
| Polyetheramine MW230-4000 | 0-20% | 0-15% | 0-10% |
| Diol Chain Extender | 0.1-20% | 5-18% | 6-15% |
| Radiopaque Material | 10%-50% | 15-50% | 15-45% |

General Procedure for Formation of Vascular Access Devices

Vascular access devices include but are not limited to catheter tubing. Exemplary devices are: central venous catheters, peripherally-inserted central catheters, and peripheral intravenous catheters. Catheter tubing can be formed through compounding and extrusion or coextrusion processes. During the compounding, granulates of synthesized polyurethanes described herein and radiopaque filler are added into a compounder simultaneously. The mix ratio can be controlled and adjusted by a gravimetric multiple-feeder system. The mixed polyurethane melt continuously passes through a die in the front of the compounder, passes through a quench tank, and is cut into regular-sized pellets by a puller-pelletizer. The collected pellets are used to be fed into an extruder/coextruder to form a catheter tube, depending on tubing's specific configuration.

Embodiments of catheter tubing based on polyurethanes discussed herein can be varied by changing and selecting of extruder/coextruders, extrusion dies, the number of stripes and layers, the volume percentage of stripe material and the type of radiopaque agent.

Figure 1:
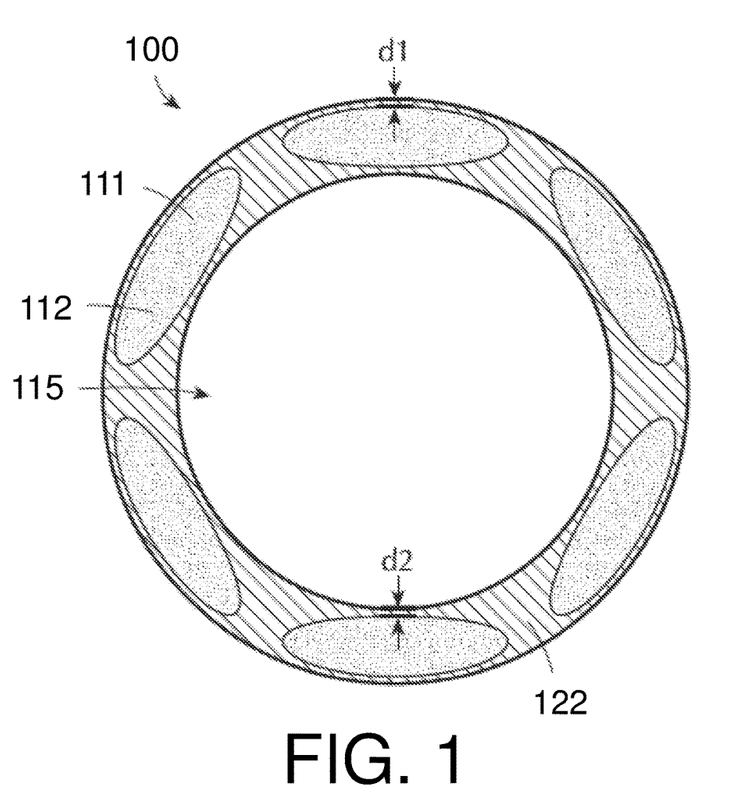
FIG. 1 provides a schematic cross-section view of an exemplary vascular access device.

Turning to the figures, FIG. 1 provides a schematic cross-section of an exemplary vascular access device in the form of catheter tubing 100, which comprises a body 122 of a base polyurethane and one or more stripes 112 of a compounded polyurethane throughout the body 122. The body 122 is clear and the stripes 112 are opaque and positioned to permit visual feedback in the areas of the catheter body 122 where there are not stripes. The compounded polyurethane of the stripes 112 may according to any of the exemplary formulations of Table 2, including radiopaque material(s) 111. The stripe 112 may include the same base polyurethane as body 122 or the stripe 112 may include a different polyurethane compared to the base polyurethane of body 122. The stripes 112 are generally elongate along the tubing. In this embodiment, there are six stripes 112 of oval cross-section, which are substantially evenly distributed throughout the body 122. Distance of the stripe to the tubing outer surface is d1 and distance of the stripe to the tubing inner surface is d2. The stripes 112 in one or more embodiments are spaced to be equidistant between the tubing inner and outer surfaces (d1=d2). The body 122 defines a lumen 115. To form the striped tubing of FIG. 1, the compounded polyurethane is coextruded with the base polyurethane and processed through a cross-head die to form an integral tubing having stripes.

In one or more embodiments, a cross-sectional area of the tubing comprises the base thermoplastic polyurethane in an amount in the range of 60% to 80% and the compounded thermoplastic polyurethane in an amount in the range of 20% to 40%. In an embodiment, the cross-sectional area comprises 35±3% stripes. In another embodiment, the cross-sectional area comprises 25±3% stripes.

The catheter tubing disclosed herein demonstrates a first elastic modulus under first conditions prior to entry into a patient. The first elastic modulus may be at least 500 MPa, or 600 MPa, or 700 MPa, or 800 MPa, or 900 MPa, or 1000 MPa, or 1100 MPa, or 1200 MPa, or 1300 MPa or greater. The first elastic modulus may be in the range of 500 to 2200 MPa or 1300 MPa to 2200 MPa.

The catheter tubing disclosed herein demonstrates a second elastic modulus after exposure for a duration to second conditions comprising two or more in vivo stimuli after to entry into a patient. The second elastic modulus is not more than fifty percent of the first modulus. That is, the second elastic modulus is reduced by more than fifty percent after exposure to the second conditions for a duration. The second elastic modulus may be at most 650 MPa, or 600 MPa, or 550 MPa, or 500 MPa, or 450 MPa, or 400 MPa, or 350 MPa, or 300 MPa, or 250 MPa, or 200 MPa, or 150 MPa, or 100 MPa, or 50 MPa, or 10 MPa, or less. The second elastic modulus may be in the range of 10 to 650 MPa and ranges and sub-ranges in between. The second elastic modulus may be reached after a duration of about 30 minutes or less, 25 minutes or less, 20 minutes or less, 15 minutes or less, or 10 minutes or less. The second elastic modulus may be reached after a duration in the range of about 5 to 30 minutes, about 5 to 25 minutes, about 5 to 20 minutes, or about 5 to 10 minutes.

Figure 2:
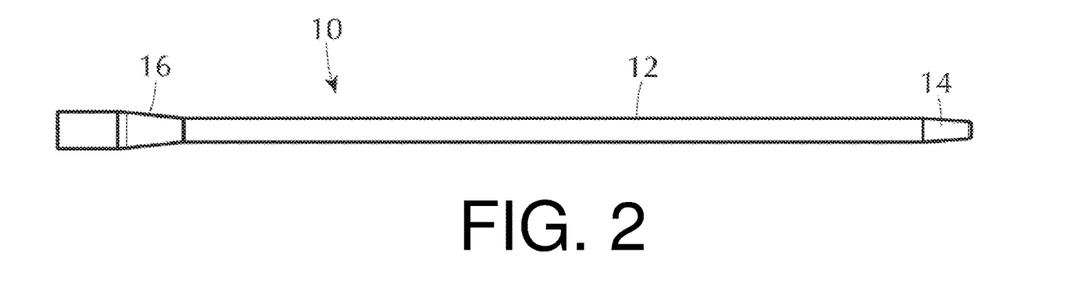
FIG. 2 is plan view of an exemplary catheter.

In FIG. 2, an exemplary catheter is illustrated. Catheter tubing as disclosed herein forms the catheter, which is shaped as needed to receive other components for forming vascular access devices. Catheter 10 comprises a primary conduit 12, which is tubing in its as-extruded form. At a distal end, a tip 14 is formed by a tipping process. At a proximal end, a flange 16 is formed as needed for receipt of other components including but not limited to catheter adapters. Exemplary vascular access devices may include a needle further to the catheter for access to blood vessels.

EMBODIMENTS

Various embodiments are listed below. It will be understood that the embodiments listed below may be combined with all aspects and other embodiments in accordance with the scope of the invention.

Embodiment 1

A catheter tubing comprising: an elongate body comprising a base thermoplastic polyurethane; and a compounded thermoplastic polyurethane co-extruded with the base thermoplastic polyurethane to provide a section of catheter tubing discrete from the elongate body, the compounded thermoplastic polyurethane comprising a thermoplastic polyurethane and a radiopaque material; wherein the catheter tubing comprises a first elastic modulus under first conditions prior to entry into a patient; and wherein when exposed to second conditions comprising two or more in vivo stimuli for a time, the catheter tubing comprises a second elastic modulus that is not more than fifty percent of the first modulus.

Embodiment 2

The catheter tubing of embodiment 1, wherein the thermoplastic polyurethane of the compounded thermoplastic polyurethane is a different formulation from the base thermoplastic polyurethane.

Embodiment 3

The catheter tubing of one of embodiments 1 to 2, wherein the section discrete from the elongate body comprises one or more elongate stripes comprising the compounded thermoplastic polyurethane, integrally formed with the elongate body.

Embodiment 4

The catheter tubing of one of embodiments 1 to 3 having a cross-sectional area that comprises the base thermoplastic polyurethane in an amount in the range of 60% to 80% and the compounded thermoplastic polyurethane in an amount in the range of 20% to 40%.

Embodiment 5

The catheter tubing of one of embodiments 1 to 4, wherein the first conditions comprise: a temperature in the range of 20 to 30° C. and a relative humidity in the range of 0 to 90%.

Embodiment 6

The catheter tubing of one of embodiments 1 to 5, wherein the first elastic modulus is at least 1300 MPa.

Embodiment 7

The catheter tubing of one of embodiments 1 to 6, wherein the first elastic modulus is the range of 1300 to 2200 MPa.

Embodiment 8

The catheter tubing of one of embodiments 1 to 7, wherein the two or more in vivo stimuli of the second conditions comprise a temperature in the range of about 36 to about 40° C., and one or more of: saline, plasma, white blood cells, platelets, red blood cells, water, absence of light, antibodies, and enzymes.

Embodiment 9

The catheter tubing of one of embodiments 1 to 8, wherein the second elastic modulus is at most 650 MPa, at most 400 MPa, at most 200 MPa, or at most 100 MPa.

Embodiment 10

The catheter tubing of one of embodiments 1 to 9, wherein the second elastic modulus is the range of 10 to 650 MPa, 10 to 400 MPa, 10 to 200 MPa, or 10 to 100 MPa.

Embodiment 11

The catheter tubing of one of embodiments 1 to 10, wherein the second elastic modulus is reached after exposure to the second conditions for about 30 minutes or less.

Embodiment 12

The catheter tubing of embodiment 11, wherein the second elastic modulus is reached after exposure to the second conditions for about 5 to about 10 minutes.

Embodiment 13

The catheter tubing of one of embodiments 1 to 12, wherein the radiopaque material of the compounded thermoplastic polyurethane comprises bismuth oxychloride (BiOCl), bismuth trioxide ($Bi_2O_3$), bismuth subcarbonate ($Bi_2O_2CO_3$), barium sulfate ($BaSO_4$), tungsten (W), or combinations thereof.

Embodiment 14

The catheter tubing of one of embodiments 1 to 13, wherein the base thermoplastic polyurethane, the compounded thermoplastic polyurethane, or both further comprise an antithrombogenic agent, an antimicrobial agent, a lubricant, a colorant, an active pharmaceutical, or combinations thereof.

Embodiment 15

A catheter tubing comprising: an elongate body comprising a base thermoplastic polyurethane that is a product from a reaction of: a diisocyanate, a diol chain extender, at least one polyglycol, and optionally, an amine-terminated polyether, the base thermoplastic polyurethane optionally further comprising an antithrombogenic agent, an antimicrobial agent, a lubricant, a colorant, an active pharmaceutical, or combinations thereof; and one or more elongate stripes co-extruded with the base thermoplastic polyurethane, the elongate stripes comprising a compounded thermoplastic polyurethane comprising a thermoplastic polyurethane and a radiopaque material; wherein the catheter tubing comprises a first elastic modulus under first conditions prior to entry into a patient; and wherein when exposed to second conditions comprising two or more in vivo stimuli for a time, the catheter tubing comprises a second elastic modulus that is not more than fifty percent of the first modulus.

Embodiment 16

The catheter tubing of embodiment 15, wherein the first conditions comprise: a temperature in the range of 20 to 30° C. and a relative humidity in the range of 0 to 90% and the two or more in vivo stimuli of the second conditions comprise a temperature in the range of about 36 to about 40° C., and one or more of: saline, plasma, white blood cells, platelets, red blood cells, water, absence of light, antibodies, and enzymes.

Embodiment 17

The catheter tubing of one of embodiments 15 to 16, wherein the first elastic modulus is the range of 1300 to 2200 MPa; and the second elastic modulus is the range of 10 to 650 MPa, 10 to 400 MPa, 10 to 200 MPa, or 10 to 100 MPa.

Embodiment 18

The catheter tubing of one of embodiments 15 to 17, wherein the second elastic modulus is reached after exposure to the second conditions for about 30 minutes or less.

Embodiment 19

The catheter tubing of embodiment 18, wherein the second elastic modulus is reached after exposure to the second conditions for about 5 to about 10 minutes.

Embodiment 20

A vascular access device comprising the catheter tubing of one of embodiments 1 to 19 in combination with one or more components, wherein the vascular access device is selected from the group consisting of: a central venous catheter, a peripherally-inserted central catheter, a midline catheter, and a peripheral intravenous catheter.

Embodiment 21

A method of making a medical device including a catheter tubing comprising: designing an elongate body having a section of catheter tubing discrete from the elongate body to form the catheter tubing such that the catheter tubing comprises a first elastic modulus under first conditions prior to entry into a patient; and wherein when exposed to second conditions comprising two or more in vivo stimuli for a time, the catheter tubing comprises a second elastic modulus that is not more than fifty percent of the first modulus.

Embodiment 22

The method of embodiment 21 wherein the designing of the elongate body having the section of catheter tubing discrete from the elongate body comprises: providing a base polyurethane; providing a compounded polyurethane comprising a thermoplastic polyurethane and a radiopaque material; and co-extruding the base polyurethane and the compounded polyurethane to form the elongate body of the base polyurethane and the section discrete from the elongate body of the compounded thermoplastic polyurethane.

Embodiment 23

The method of one of embodiments 21 to 22 further comprising combining the catheter tubing with one or more components to form the medical device.

Embodiment 24

The method of embodiment 23, wherein the one or more components includes a needle and the medical device is a vascular access device.

Embodiment 25

The method of embodiment 24, wherein the vascular access device is selected from the group consisting of: a central venous catheter, a peripherally-inserted central catheter, a midline catheter, and a peripheral intravenous catheter.

Embodiment 26

A method of delivering a medical fluid to a patient comprising: obtaining a catheter tubing; inserting the catheter tubing into a patient under first conditions when the catheter tubing comprises a first elastic modulus; and indwelling the catheter tubing for a duration under second conditions when the catheter tubing is exposed to two or more in vivo stimuli and the catheter tubing comprises a second elastic modulus that is not more than fifty percent of the first modulus.

Embodiment 27

The method of embodiment 26, wherein the catheter tubing comprises: an elongate body comprising a base thermoplastic polyurethane; and one or more sections discrete from the elongate body comprising a compounded polyurethane comprising a thermoplastic polyurethane and a radiopaque material.

Embodiment 28

The method of one of embodiments 26 to 27, wherein the first conditions comprise: a temperature in the range of 20 to 30° C. and a relative humidity in the range of 0 to 90% and the two or more in vivo stimuli of the second conditions comprise a temperature in the range of about 36 to about 40° C., and one or more of: saline, plasma, white blood cells, platelets, red blood cells, water, absence of light, antibodies, and enzymes.

Embodiment 29

The method of one of embodiments 26 to 28, wherein the first elastic modulus is the range of 1300 to 2200 MPa and the second elastic modulus is the range of 10 to 650 MPa, 10 to 400 MPa, 10 to 200 MPa, or 10 to 100 MPa.

Embodiment 30

The method of one of embodiments 26 to 29, wherein the second elastic modulus is reached after exposure to the second conditions for about 5 to about 10 minutes.

EXAMPLES

Composite catheter tubing according to Comparative Examples A-C and inventive Examples 1-3 was made by the following procedure. A first melt stream of a first base polyurethane from a primary extruder and a second melt stream of a compounded polyurethane from a secondary extruder were maintained separately until combined as continuous layers in a forward, downstream portion of an extruder head. From the extruder head, the streams subsequently passed through and emerged from a tube die (coaxial or cross-head) as an integral tubing member. The encapsulated stripes were made from the compounded polyurethane and the rest of the tubing body was made from the first base polyurethane only. The geometries of COMPARATIVE Examples A-C and Examples 1-3 were identical. The compounded polyurethane of the stripes were identical among Examples 1-3. The base polyurethane of the tubing bodies varied among Examples 1-3.

A Dynamic Mechanical Analyzer (DMA) from TA Instrument model Q800 was used to measure elastic modulus.

Comparative Example A

A commercially-available aromatic polyether polyurethane was used as a first base polyurethane, having a hard segment content of about 60% by weight. A slab of the first base polyurethane was ground into granulates, which were then converted to pellets by a traditional conventional compounding machine to result in a transparent polyurethane.

A compounded polyurethane was made from the first base polyurethane in combination with a radiopaque material. A slab of the first base polyurethane was ground into granulates, which were then compounded with barium sulfate by a traditional conventional compounding machine to result in a compounded polyurethane that was radiopaque.

In this example, the body and the stripes contained the same underlying polyurethane material. A composite catheter having a body and stripes was then fabricated.

Comparative Example B

The commercially-available polyurethane of COMPARATIVE Example A was used as a first base polyurethane.

A compounded polyurethane was made from the first base polyurethane in combination with a radiopaque material, and an additive to increase stiffness. A slab of the first base polyurethane was ground into granulates, which were then compounded with both the additive and barium sulfate by a traditional conventional compounding machine to result in a compounded polyurethane that was radiopaque.

In this example, the body and the stripes contained the same underlying polyurethane materials. A composite catheter having a body and stripes was then fabricated.

Comparative Example C

The commercially-available polyurethane of COMPARATIVE Example A was used as a first base polyurethane.

A compounded polyurethane was made from a second base polyurethane and a radiopaque material. The second base polyurethane was different from the first base polyurethane in that it had about 70% hard segment. A slab of the second base polyurethane was ground into granulates, which were then compounded with barium sulfate by a traditional conventional compounding machine to result in a compounded polyurethane that was radiopaque.

In this example, the body and the stripes contained different underlying polyurethane materials. A composite catheter having a body and stripes was then fabricated.

Comparative Example D

A commercially-available striped hexafluoropropylene and tetrafluoroethylene (FEP) catheter tubing was obtained.

Example 1

A first base polyurethane was made by the "one shot" bulk polymerization process (no catalyst) in accordance with Exemplary Formulation C as shown in Table 1 using MDI as the aromatic diisocyanate with and the polyglycol PTMEG of varying molecular weights (Nominal MW<1000 and Nominal 1000≥MW≤2900). The chain extender was 1,4 butanediol. A slab of the first base polyurethane was ground into granulates, which were then converted to pellets by a traditional conventional compounding machine to result in a transparent polyurethane.

A compounded polyurethane was made from a second base polyurethane and a radiopaque material. The second base polyurethane was made by the "one shot" bulk polymerization process (no catalyst), utilizing MDI as the aromatic diisocyanate and the polyglycol PTMEG with a wider PTMEG molecular weight distribution relative to the first base polyurethane and 1,4 butanediol as the chain extender. A slab of the second base polyurethane was ground into granulates, which were then compounded with barium sulfate by a traditional conventional compounding machine to result in a compounded polyurethane that was radiopaque.

In this example, the body and the stripes contained different underlying polyurethane materials. A composite catheter having a body and stripes was then fabricated according to the procedure provided above.

Example 2

The second base polyurethane of Example 1 as used as a first base polyurethane in Example 2.

The compounded polyurethane of Example 2 was the same as that of Example 1.

In this example, the body and the stripes contained the same underlying polyurethane material. A composite catheter having a body of the first base polyurethane and stripes of the compounded polyurethane was then fabricated according to the procedure provided above.

Example 3

The commercially-available polyurethane of COMPARATIVE Example A was used as a first base polyurethane.

The compounded polyurethane of Example 3 was the same as that of Examples 1-2.

In this example, the body and the stripes contained different underlying polyurethane materials. A composite catheter having a body of the first base polyurethane and stripes of the compounded polyurethane was then fabricated according to the procedure provided above.

Example 4

Testing

Elastic modulus of tubing according to Comparative Examples A-D and Inventive Examples 1-3 was measured under environmental temperatures (25° C. and 30° C.) and various nominal relative humidity (RH) values, the results for which are summarized in Tables 3-4.

TABLE 3

Modulus at Insertion 25° C.

| EXAMPLE | 20% RH MPa | 40% RH MPa | 60% RH MPa | 90% RH MPa |
|---|---|---|---|---|
| Example 1 | 2015 | 1828 | 1559 | 1062 |
| Example 2 | 1749 | 1653 | 1506 | 1162 |
| Example 3 | 1429 | 1328 | 1191 | 926 |
| Comparative Example A | 566 | 515 | 446 | 335 |
| Comparative Example B | 1042 | 967 | 863 | 663 |
| Comparative Example C | 1228 | 1154 | 1046 | 926 |
| Comparative Example D | 445 | 446 | 446 | 445 |

TABLE 4

Modulus at Insertion 30° C.

| EXAMPLE | 20% RH MPa | 40% RH MPa | 60% RH MPa | 90% RH MPa |
|---|---|---|---|---|
| Example 1 | 1373 | 1085 | 772 | 320 |
| Example 2 | 1467 | 1267 | 1025 | 638 |
| Example 3 | 2263 | 1018 | 853 | 560 |
| Comparative Example A | 472 | 393 | 322 | 218 |
| Comparative Example B | 867 | 754 | 649 | 432 |
| Comparative Example C | 849 | 754 | 649 | 476 |
| Comparative Example D | 583 | 580 | 579 | 579 |

The results of Tables 3-4 indicate a substantially linear response of elastic modulus as changing with respect to a single variable, namely relative humidity. For Examples 1-3 and A-C, as relative humidity increases, the elastic modulus decreases. For Example D, there is not a significant change in elastic modulus over different relative humidity values.

Elastic modulus results of tubing according to Comparative Examples A-D and Inventive Examples 1-3 under varying temperatures (25° C., 30° C., 35° C., and 40° C.) and 0% relative humidity are summarized in Table 5.

TABLE 5

Modulus at Various Temperatures 0% RH

| EXAMPLE | 25° C. MPa | 30° C. MPa | 35° C. MPa | 40° C. MPa |
|---|---|---|---|---|
| Example 1 | 2129 | 1587 | 1249 | 904 |
| Example 2 | 1811 | 1614 | 1464 | 1112 |
| Example 3 | 1491 | 1237 | 1178 | 904 |
| Comparative Example A | 572 | 537 | 469 | 434 |
| Comparative Example B | 1061 | 989 | 813 | 728 |
| Comparative Example C | 1239 | 929 | 834 | 734 |
| Comparative Example D | 439 | 587 | 501 | 564 |

The results of Table 5 indicate varying responses of elastic modulus as changing with respect to a single variable, namely temperature. For Examples 1-3 and A-C, as temperature increases, the elastic modulus decreases. For Example D, the change in elastic modulus over different temperatures is not linear.

Elastic modulus results of tubing according to Comparative Examples A-D and Inventive Examples 1-3 under various recommended storage conditions (for real-time studies) as defined by climatic zones by World Health Organization (WHO) are summarized in Table 6.

TABLE 6

| EXAMPLE | Zone II 25° C. 60% RH MPa | Zone III 30° C. 35% RH* MPa | Zone IV 30° C. 70% RH MPa |
|---|---|---|---|
| Example 1 | 1559 | 1085 | 614 |
| Example 2 | 1506 | 1267 | 897 |
| Example 3 | 1191 | 1019 | 761 |
| Comparative Example A | 447 | 393 | 290 |
| Comparative Example B | 863 | 755 | 576 |
| Comparative Example C | 1046 | 754 | 594 |
| Comparative Example D | 446 | 580 | 579 |

*Zone III is defined as 30° C. 35% RH. Data was collected at 40% RH due to parameters of testing equipment.

The results of Table 6 demonstrate the widely varying elastic modulus based on storage conditions. Stiffness for insertion can therefore vary widely depending on conditions that catheters are exposed to prior to insertion.

Example 5

Testing

Elastic modulus of tubing according to Comparative Examples A-D and Inventive Examples 1-3 was measured after exposure to a single in vivo stimulus for a duration of time, the results for which are summarized in Table 7. In Table 7, time 0 corresponds to when the saline in which the tubing was soaking achieved steady state 25° C.

TABLE 7

Modulus at Indwell (single stimulus pre-priming) 25° C.

| EXAMPLE | 0 minutes MPa | 6 minutes MPa | 10 minutes MPa |
|---|---|---|---|
| Example 1 | 2233 | 1944 | 1790 |
| Example 2 | 1202 | 805 | 667 |
| Example 3 | 1070 | 712 | 569 |
| Comparative Example A | 462 | 286 | 221 |
| Comparative Example B | 770 | 532 | 430 |
| Comparative Example C | 809 | 601 | 509 |
| Comparative Example D | 445 | 455 | 456 |

The results of Table 7 show modest softening over time for Examples 1-3. Comparative Examples A-C also modestly soften over time. Comparative Example D shows no significant change.

Example 6

Testing

Elastic modulus of tubing according to Comparative Examples A-D and Inventive Examples 1-3 was measured after exposure to two in vivo stimuli for a duration of time, the results for which are summarized in Table 8. In Table 8, time 0 corresponds to when the saline in which the tubing was soaking achieved steady state 37° C.

TABLE 8

Modulus at Indwell (Soaked in 37° C. Saline)

| EXAMPLE | 0 minutes MPa | 5 minutes MPa | 15 minutes MPa | 30 minutes MPa |
|---|---|---|---|---|
| Example 1 | 805 | 203 | 38 | 26 |
| Example 2 | 740 | 231 | 61 | 52 |
| Example 3 | 688 | 245 | 81 | 61 |
| Comparative Example A | 128 | 115 | 109 | 106 |
| Comparative Example B | 230 | 151 | 137 | 130 |
| Comparative Example C | 497 | 283 | 206 | 192 |
| Comparative Example D | 468 | 466 | 471 | 473 |

The results of Table 8 show that Examples 1-3 have significant softening in a relatively short duration of time when exposed to two in vivo stimuli. That is, a non-linear response is achieved with the inventive tubing. It is advantageous to have catheter materials that reduce their modulus only upon exposure to multiple stimuli that are unique to the human veins. In Examples 1-3 the presence of both stimuli (37° C. and saline) are required for the modulus to decrease. Comparative Example D shows no significant change upon exposure to multiple stimuli. Comparative Examples A-B show only a modest reduction in elastic modulus. Comparative Example C shows softening but not as quickly as Examples 1-3. The examples achieved steady state after about 30 minutes of indwelling.

Overall, the higher modulus at all insertion environments (pre-prime and humidity) of Inventive Examples 1-3 ensure higher likelihood of insertion success while the softer modulus when exposed to more than one stimulus in the body environment will facilitate a reduction in catheter-related complications like phlebitis, infiltration, and extravasation.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A catheter tubing comprising:
an elongate body comprising a base thermoplastic polyurethane; and
a compounded thermoplastic polyurethane co-extruded with the base thermoplastic polyurethane to provide a section of catheter tubing discrete from the elongate body, the compounded thermoplastic polyurethane comprising a thermoplastic polyurethane and a radiopaque material;
wherein the catheter tubing comprises a first elastic modulus under first conditions prior to entry into a patient;
wherein when exposed to second conditions comprising two or more in vivo stimuli for a time, the catheter tubing comprises a second elastic modulus that is not more than fifty percent of the first elastic modulus; and
wherein the first elastic modulus is a minimum of 1300 MPa.

2. The catheter tubing of claim 1, wherein the thermoplastic polyurethane of the compounded thermoplastic polyurethane is a different formulation from the base thermoplastic polyurethane.

3. The catheter tubing of claim 1, wherein the section discrete from the elongate body comprises one or more elongate stripes comprising the compounded thermoplastic polyurethane, integrally formed with the elongate body.

4. The catheter tubing of claim 1 having a cross-sectional area that comprises the base thermoplastic polyurethane in an amount in the range of 60% to 80% and the compounded thermoplastic polyurethane in an amount in the range of 20% to 40%.

5. The catheter tubing of claim 1, wherein the first conditions comprise: a temperature in a range of 20 to 30° C. and a relative humidity in a range of 0 to 90%.

6. The catheter tubing of claim 1, wherein the first elastic modulus is the range of 1300 to 2200 MPa.

7. The catheter tubing of claim 1, wherein the two or more in vivo stimuli of the second conditions comprise a temperature in the range of about 36 to about 40° C., and one or more of: saline, plasma, white blood cells, platelets, red blood cells, water, absence of light, antibodies, and enzymes.

8. The catheter tubing of claim 1, wherein the second elastic modulus is a maximum of 650 MPa.

9. The catheter tubing of claim 8, wherein the second elastic modulus is the range of 10 to 650 MPa.

10. The catheter tubing of claim 1, wherein the second elastic modulus is reached after exposure to the second conditions for about 30 minutes or less.

11. The catheter tubing of claim 10, wherein the second elastic modulus is reached after exposure to the second conditions for about 5 to about 10 minutes.

12. The catheter tubing of claim 1, wherein the radiopaque material of the compounded thermoplastic polyurethane comprises bismuth oxychloride (BiOCl), bismuth trioxide ($Bi_2O_3$), bismuth subcarbonate ($Bi_2O_2CO_3$), barium sulfate ($BaSO_4$), tungsten (W), or combinations thereof.

13. The catheter tubing of claim 1, wherein the base thermoplastic polyurethane, the compounded thermoplastic polyurethane, or both further comprise an antithrombogenic agent, an antimicrobial agent, a lubricant, a colorant, an active pharmaceutical, or combinations thereof.

14. A vascular access device comprising the catheter tubing of claim 1 in combination with one or more components, wherein the vascular access device is selected from the group consisting of: a central venous catheter, a peripherally-inserted central catheter, a midline catheter, and a peripheral intravenous catheter.

15. The catheter tubing of claim 1, wherein the base thermoplastic polyurethane is a product from a reaction of: a diisocyanate, a diol chain extender, and at least one polyglycol, and optionally further, an amine-terminated polyether.

16. A catheter tubing comprising:
an elongate body comprising a base thermoplastic polyurethane that is a product from a reaction of: a diisocyanate, a diol chain extender, and at least one polyglycol, and optionally further, an amine-terminated polyether; and optionally the base thermoplastic polyurethane further comprises an antithrombogenic agent, an antimicrobial agent, a lubricant, a colorant, an active pharmaceutical, or combinations thereof; and
one or more elongate stripes co-extruded with the base thermoplastic polyurethane, the elongate stripes comprising a compounded thermoplastic polyurethane comprising a thermoplastic polyurethane and a radiopaque material;
wherein the catheter tubing comprises a first elastic modulus under first conditions prior to entry into a patient; and
wherein when exposed to second conditions comprising two or more in vivo stimuli for a time, the catheter tubing comprises a second elastic modulus that is not more than fifty percent of the first elastic modulus; and
wherein the first elastic modulus is the range of 1300 to 2200 MPa.

17. The catheter tubing of claim 16, wherein the first conditions comprise: a temperature in a range of 20 to 30° C. and a relative humidity in a range of 0 to 90% and the two or more in vivo stimuli of the second conditions comprise a temperature in the range of about 36 to about 40° C., and one or more of: saline, plasma, white blood cells, platelets, red blood cells, water, absence of light, antibodies, and enzymes.

18. The catheter tubing of claim 16, wherein the second elastic modulus is the range of 10 to 650 MPa.

19. The catheter tubing of claim 16, wherein the second elastic modulus is reached after exposure to the second conditions for about 30 minutes or less.

20. The catheter tubing of claim 19, wherein the second elastic modulus is reached after exposure to the second conditions from about 5 to about 10 minutes.

21. The catheter tubing of claim 16, wherein the at least one polyglycol is a polytetramethylene ether glycol (PTMEG).

* * * * *